US010112891B2

(12) United States Patent
Grammenos et al.

(10) Patent No.: US 10,112,891 B2
(45) Date of Patent: Oct. 30, 2018

(54) STEREOSELECTIVE PROCESS TO OBTAIN (Z)-5-CYCLYLOXY-2-[(E)-METHOXYIMINO]-3-METHYL-PENT-3-ENIC ACID METHYL AMIDES USING E,Z-ISOMER MIXTURE OF AND INTERMEDIATES THEREOF

(71) Applicant: BASF SE, Ludwigshafen (DE)

(72) Inventors: Wassilios Grammenos, Ludwigshafen (DE); Ana Escribano Cuesta, Mannheim (DE); Ian Robert Craig, Ludwigshafen (DE); Joachim Rheinheimer, Ludwigshafen (DE); Christian Winter, Ludwigshafen (DE); Michael Rack, Eppelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/517,352

(22) PCT Filed: Oct. 5, 2015

(86) PCT No.: PCT/EP2015/072909
§ 371 (c)(1),
(2) Date: Apr. 6, 2017

(87) PCT Pub. No.: WO2016/055404
PCT Pub. Date: Apr. 14, 2016

(65) Prior Publication Data
US 2017/0298012 A1    Oct. 19, 2017

(30) Foreign Application Priority Data
Apr. 24, 2015    (EP) .................................... 15165054

(51) Int. Cl.
| C07C 249/12 | (2006.01) |
| C07D 309/32 | (2006.01) |
| C07D 309/38 | (2006.01) |
| C07D 231/22 | (2006.01) |
| C07C 251/40 | (2006.01) |

(52) U.S. Cl.
CPC .......... *C07C 249/12* (2013.01); *C07C 251/40* (2013.01); *C07D 231/22* (2013.01); *C07D 309/32* (2013.01); *C07D 309/38* (2013.01)

(58) Field of Classification Search
CPC ... C07C 249/12; C07C 251/40; C07D 231/22; C07D 309/32; C07D 309/38
See application file for complete search history.

(56) References Cited

U.S. PATENT DOCUMENTS 5,346,898 A    9/1994    Cooper et al.

FOREIGN PATENT DOCUMENTS

| WO | 96/07635 | 3/1996 |
| WO | 2013/092224 | 6/2013 |
| WO | WO2013092224 | * 6/2013 |
| WO | 2014/202421 | 12/2014 |
| WO | 2016/142224 | 9/2016 |

OTHER PUBLICATIONS

Bicknell, et al., "Novel Phosphorane and Phosphonate Synthons for Vinyl Glycines", Tetrahedron Letters, vol. 29, Issue 27, 1988, pp. 3361-3364.
Diaz-Rodriguez, et al., "From Diols to Lactones under Aerobic Conditions using a Laccase/TEMPO Catalytic System in Aqueous Medium", Advanced Synthesis & Catalysis, vol. 354, I.
Fukuzawa, et al., "Ruthenium-Catalyzed Reduction of N-Alkoxy- and N-Hydroxyamides", Journal of Organometallic Chemistry, vol. 696, Issue 23, Nov. 15, 2011, pp. 3643-3648.
International Preliminary Report on Patentability for PCT Patent Application No. PCT/EP2015/072909, dated Apr. 20, 2017, 7 pages.
International Search Report and Written Opinion for PCT Patent Application No. PCT/EP2015/072909, dated Jan. 12, 2016, 10 pages.
Kuang, et al., "Room-Temperature Debenzylation of N-Benzylcarboxamides by N-Bromosuccinimide", Synthesis, Issue 20, 2007, pp. 3129-3134.
Li, et al., "Study on Synthesis and Bacteriostatic Activity of 2-methoxyimino-2-(2-(substituted phenyl)-N-methylacetamide derivatives containing double oxime ether structures . . . " Journal of Nanjing Agricultural University, 2012, 35(2), pp. 141-145.
Li, et al., "Synthesis and Antifungal Bioactivity of Methyl 2-Methoxyimino-2-(2-[(substituted benzylidene)aminooxymethyl]phenyl}acetate and 2-Methoxyimino-2-{2-[(substituted benzylidene)aminooxymethyl]phenyl}-N-methylacetamide Derivatives", Chinese Journal of Chemistry, 2009, 27, pp. 2055-2060.
Ohmura, et al., "Hydrolytic Deallylation of N-Allyl Amides Catalyzed by PdII Complexes", European Journal of Organic Chemistry, vol. 2008, Issue 30, Oct. 2008, pp. 5042-504.
Reetz, et al., "Copper-Catalyzed Enantioselective Conjugate Addition of Diethylzinc to α,β-Unsaturated Carbonyl Compounds Using Diphosphonites as Chiral Ligands", Tetrahedron Letters 43 (2002) 1189-1191.
Reggelin, et al., "Metallated 2-Alkenyl Sulfoximines in Asymmetric Synthesis: Regio- and Stereoselective Synthesis of Highly Substituted Oxabicyclic Ethers and Studies Towards the Total Syntheses
(Continued)

*Primary Examiner* — Pancham Bakshi
*Assistant Examiner* — Mark R Luderer
(74) *Attorney, Agent, or Firm* — Brinks Gilson & Lione

(57) ABSTRACT

The present invention relates to a process for preparation of intermediates (Z,2E)-5-hydroxy-2-methoxyimino-N-methyl-pent-3-enamides from 4-substituted 5-meth-oxy-imino-2H-pyran-6-ones and their processing for example to (Z)-5-cyclyloxy-2-[(E)-methoxyimino]-3-methyl-pent-3-enic acid methyl amides. The invention also relates to a process for preparation of 4-substituted 5-imino-2H-pyran-6-ones and to novel intermediates for the preparation of fungicidal (Z)-5-cyclyloxy-2-[(E)-methoxyimino]-3-methyl-pent-3-enic acid methyl amides.

17 Claims, No Drawings

(56) References Cited

OTHER PUBLICATIONS of the Euglobals G1 and G2 and Arenaran A", Eur. J. Org. Chem. 1999, 1011-1031.
Williams, et al., "Carbanion-Mediated Oxidative Deprotection of Non-Enolizable Benzylated Amides", Tetrahedron Letters, vol. 30, Issue 4, 1989, pp. 451-454.

* cited by examiner

STEREOSELECTIVE PROCESS TO OBTAIN (Z)-5-CYCLYLOXY-2-[(E)-METHOXYIMINO]-3-METHYL-PENT-3-ENIC ACID METHYL AMIDES USING E,Z-ISOMER MIXTURE OF AND INTERMEDIATES THEREOF

This application is a National Stage application of International Application No. PCT/EP2015/072909 filed Oct. 5, 2015. This application also claims priority under 35 U.S.C. § 119 to European Patent Application No. 14188508.7, filed Oct. 10, 2014 and European Patent Application No. 15165054.6 filed Apr. 24, 2015.

DESCRIPTION

The present invention relates to a process for preparation of intermediates (Z,2E)-5-hydroxy-2-methoxyimino-N-methyl-pent-3-enamides from 4-substituted 5-methoxy-imino-2H-pyran-6-ones and their processing for example to (Z)-5-cyclyloxy-2-[(E)-methoxyimino]-3-methyl-pent-3-enic acid methyl amides. The invention also relates to a process for preparation of 4-substituted 5-imino-2H-pyran-6-ones and to novel intermediates for the preparation of fungicidal (Z)-5-cyclyloxy-2-[(E)-methoxyimino]-3-methyl-pent-3-enic acid methyl amides.

(Z)-5-cyclyloxy-2-[(E)-methoxyimino]-3-methyl-pent-3-enic acid methyl amides are known as fungicides from WO 2013/092224. The preparation of such (Z)-5-cyclyloxy-2-[(E)-methoxy-imino]-3-methyl-pent-3-enic acid methyl amides is described in the abovementioned reference using a Wittig-Horner reaction (see also Tetrahedron Lett. 29, 3361, 19881

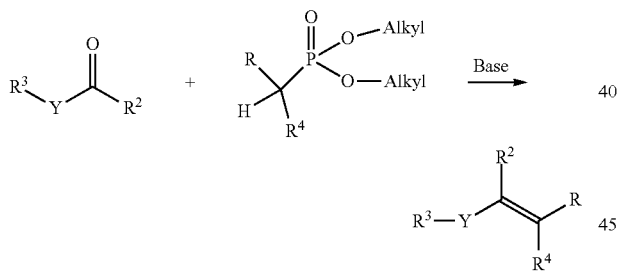

using substituted aldehydes and dialkoxyphosphoryl compounds.

This reaction resulted in substantial amounts (80%, see Example 4b in WO 2013/092224) of the undesired E-isomer based on the C═C double bond which had to be removed by purification known in the art (e.g. chromatography, distillation, crystallization, etc.). Furthermore, this reaction of Example 4b in WO 2013/092224 required the use of the specific 2Z-isomer of the respective dialkylphosphoryl compound based on the N═O double bond to obtain the corresponding 2E-isomer product:

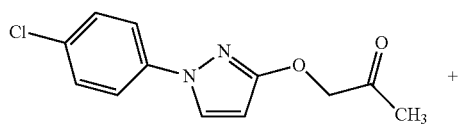

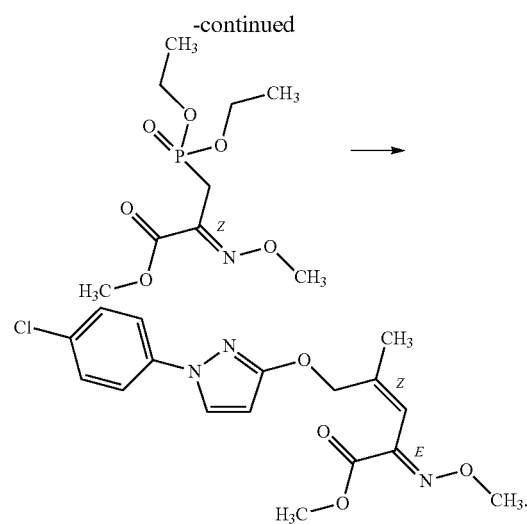

A reaction of the lactone 4-methyl-2,5-dihydropyran-6-one with N-dimethylhydroxylamine hydrochloride and trimethylaluminium in hexane to yield the corresponding ring-opened Weinreb amide has been disclosed in Eur. J. Org. Chem. 5 (1999), 1011-131.

Thus, it was an object of the present invention of overcome the disadvantages of the known process and to provide an improved, more economical and production plant friendly process via a highly stereo-selective synthesis of novel (Z,2E)-5-hydroxy-2-methoxyimino-N-methyl-pent-3-enamide intermediates using E,Z-isomer mixtures of precursor compounds.

It was surprisingly found that open chain compounds of formula I

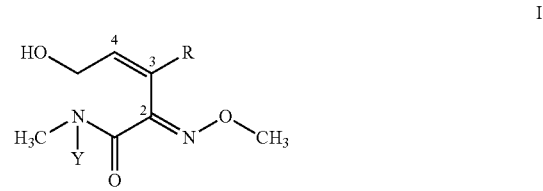

can be obtained starting from cyclic compounds of formula II

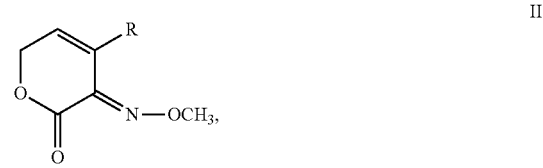

in a stereo-selective manner in that the double bond geometry of the oxime group is in E-configuration which means that the —OCH$_3$ group and the —C(═O)NYCH$_3$ group are on the opposite side of the C═N double bond between the carbon atom and the neighbouring nitrogen atom (E-configuration) and in that the double bond geometry of the C═C double bond is in Z-configuration which means the —CH$_2$—OH group and the —C(═NOCH$_3$)C(═O)

NYCH$_3$— group are on the same side of the C=C double bond between the carbon atoms depicted with the numbers 3 and 4 (Z-configuration).

Accordingly, the present invention relates to a process for preparing compounds of formula I

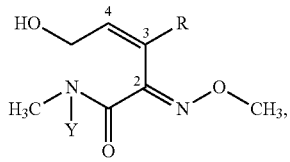

I wherein
R is C$_1$-C$_4$-alkyl, C$_1$-C$_4$-haloalkyl, C$_3$-C$_6$-cycloalkyl or C$_3$-C$_6$-cycloalkyl-C$_1$-C$_4$-alkyl;
Y is hydrogen, C$_1$-C$_4$-alkoxy, C$_2$-C$_4$-alkenyl or benzyl,
wherein the —CH$_2$—OH group and the —C(=NOCH$_3$)C(=O)NYCH$_3$ group are on the same side of the C=C double bond between the carbon atoms depicted with the numbers 3 and 4 (Z-configuration), and
wherein the —OCH$_3$ group and the —C(=O)NYCH$_3$ group are on the opposite side of the C=N double bond between the carbon atom depicted with number 2 and the neighbouring nitrogen atom (E-configuration);
the process comprising:
reacting a compound of formula II

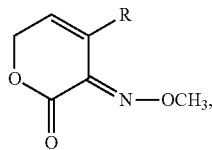

II wherein R is as defined above;
with a compound of formula III

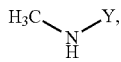

III wherein Y is as defined above;
preferably in the presence of a solvent.

Preferably, the abovementioned reaction provides a stereoselectivity of at least 9:1 (ratio of the desired (Z,2E)-isomer of compounds I versus the sum of the corresponding (E,2E)-, (E,2Z)- and (Z,2Z)-isomers of compounds I; more preferably it provides a stereoselectivity ratio of at least 95:5.

The reaction may be carried out in a wide temperature range, typically from −20° C. to 150° C. A practical temperature range is from 15° C. to 85° C. A preferred temperature range is from 20 to 70° C.; even more preferably from 40° C. to 70° C. The reaction can be carried out at pressure ranges typically from 0.3 atm to 3 atm, preferably form 0.5 atm to 2 atm, in particular at ambient pressure (0.8 to 1.5 atm).

Suitable solvents are aliphatic hydrocarbons; aromatic hydrocarbons such as toluene, o-, m- and p-xylene; halogenated hydrocarbons chlorobenzene, dichlorobenzene; ethers such as diethyl ether, diisopropyl ether, methyl tert-butyl ether (MTBE), dioxane, anisole and tetra-hydrofuran (THF); nitriles such as acetonitrile and propionitrile; alcohols such as methanol, ethanol, n-propanol, isopropanol, n-butanol and tert-butanol; and also dimethyl sulfoxide (DMSO), dimethyl-formamide (DMF), dimethyl acetamide, N-methyl-2-pyrrolidone (NMP), N-ethyl-2-pyrrolidone (NEP), acetic acid ethyl ester and water. It is also possible to use mixtures of the solvents mentioned. Particular preference is given to THF and MTBE and even more to mixtures of THF or MTBE with water.

The reaction period after addition of compound III is not particularly limited and, typically, is in the range of from 5 minutes to 24 hours, preferably from 30 minutes to 10 hours.

According to one embodiment of said process, a mixture of the E/Z-isomers of compounds of formula II is used, more preferably said mixture comprises an E/Z-isomer ratio of from 0.1:1 to 10:1, even more preferably of from 0.5:1 to 2:1.

According to another embodiment, the E-isomer of compounds of formula II is used.

According to a further embodiment, the Z-isomer of compounds of formula II is used.

The reaction mixture obtained is worked up and the compound I can be isolated in a customary manner, e.g. by an aqueous, extractive workup, by removing the solvent, e.g. under reduced pressure, or by a combination of these measures. Further purification can be effected, for example, by crystallization, distillation or by chromatography.

The amine compounds III (CH$_3$—NH—Y) are known from the literature or are commercially available.

Unless otherwise defined, the general terms used herein have the following meanings:

The term "halogen" denotes fluorine, chlorine, bromine or iodine, especially fluorine, chlorine or bromine.

The term "C$_1$-C$_4$-alkyl" denotes a linear or branched alkyl radical comprising from 1 to 4 carbon atoms, such as methyl, ethyl, propyl, 1-methylethyl (isopropyl), butyl, 1-methylpropyl (sec-butyl), 2-methylpropyl (isobutyl) or 1,1-dimethylethyl (tert-butyl).

The term "C$_1$-C$_4$-haloalkyl" denotes a linear or branched alkyl radical comprising from 1 to 4 carbon atoms (as mentioned above), where some or all of the hydrogen atoms in these groups may be replaced by halogen atoms as mentioned above: in particular C$_1$-C$_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromo-ethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

The terms "compounds I", "compounds II", "compounds III" and compounds "IV" refer to compounds of formulae I, II, III, and IV, respectively; likewise for all other formulae used herein.

In compounds of formulae I, II, IV, V, VI, VII, VIIb and VIII, R is preferably C$_1$-C$_4$-alkyl or C$_1$-C$_4$-halogenalkyl; more preferably C$_1$-C$_2$-alkyl or C$_1$-C$_2$-haloalkyl, in particular methyl. According to a further embodiment, R is C$_1$-C$_2$-halogenalkyl, in particular CF$_3$.

According to a further embodiment, Y in compounds of formulae I, III, IV and VI is allyl (prop-2-enyl), benzyl, methoxy or hydrogen.

According to a further embodiment, Y in compounds of formulae I, III, IV and VI is hydrogen.

The hydroxyl group of the compound I may be converted into leaving group such as halogen, an optionally substituted alkylsulfonyloxy group or an optionally substituted arylsulfonyloxy group to produce the compounds IV:

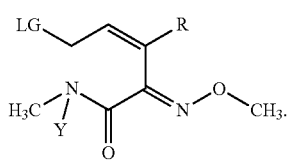

The halogen represented by LG include, for example, chlorine, bromine and iodine, preferably chlorine and bromine.

The optionally substituted alkylsulfonyloxy groups represented by LG include, for example, methanesulfonyloxy, trifluoromethanesulfonyloxy, etc. preferably methanesulfonyloxy. The optionally substituted alkylsulfonyloxy groups represented by LG are preferably $C_1$-$C_6$-alkylsulfonyloxy, wherein alkyl is unsubstituted or substituted by 1, 2, 3, 4 or 5 halogen substituents. Even more preferably the $C_1$-$C_6$-alkyl moiety in $C_1$-$C_6$-alkylsulfonyloxy is selected from methyl, ethyl, propyl, 1-methyl-ethyl, butyl, 1-methylpropyl, 2-methylpropyl (isobutyl), 1,1-dimethylethyl, pentyl, 1-methylbutyl, 2-methyl-butyl, 3-methylbutyl, 2,2-dimethylpropyl, 1-ethylpropyl, 1,1-dimethylpropyl, 1,2-dimethylprop-yl, hexyl, 1-methylpentyl, 2-methylpentyl, 3-methyl pentyl, 4-methyl-pentyl, 1,1-di-methyl-butyl, 1,2-dimethylbutyl, 1,3-dimethyl-butyl, 2,2-dimethylbutyl, 2,3-dimethylbutyl, 3,3-di-methylbutyl, 1-ethylbutyl, 2-ethylbutyl, 1,1,2-trimethylpropyl, 1,2,2-tri-methylpropyl, 1-ethyl-1-methylpropyl and 1-ethyl-2-methylpropyl. Preferably, the optionally substituted alkylsulfonyloxy is $C_1$-$C_6$-alkylsulfonyloxy, wherein the alkyl moiety is unsubstituted or one $CH_3$— group of said alkyl is substituted by 3 halogen substituents, more preferably the alkyl moiety is unsubstituted.

The optionally substituted arylsulfonyloxy groups represented by LG include, for example, p-toluenesulfonyloxy, 4-bromophenylsulfonyloxy, benzenesulfonyloxy, etc. preferably, p-toluenesulfonyloxy and benzenesulfonyloxy. The optionally substituted arylsulfonyloxy groups represented by LG are preferably selected from phenylsulfonyloxy, wherein phenyl is unsubstituted or is substituted by 1, 2, 3, 4 or 5 substituents selected from halogen, $C_1$-$C_6$-alkyl, $C_1$-$C_6$-halo-alkyl, $C_1$-$C_6$-haloalkoxy and cyclopropyl; preferably said substituents of the phenyl moiety are selected from Cl, Br, $CH_3$, $CH_2CH_3$, $CF_3$, $OCF_3$, and $OCHF_2$; more preferably phenyl is unsubstituted or is substituted by one substituent as defined above; and even more preferably phenyl is unsubstituted or is substituted by one substituent as defined above in para-position.

The conversion into compounds IV, wherein LG is halogen, can be carried out by reacting the compound I with a halogenating agent. This reaction is carried out in the absence of any solvent or in an appropriate solvent, if necessary, in the presence of a phase-transfer catalyst or base.

Suitable halogenating agents include, for example, thionyl halides (e.g., thionyl chloride, thionyl bromide, etc.), phosphoryl halides (e.g., phosphoryl chloride, phosphoryl bromide, etc.), tetrahalogenomethanes (e.g., carbon tetrachloride, carbon tetrabromide, etc.) in the presence of organic phosphorus compounds (e.g., triphenylphosphine, etc.), etc., more preferably thionyl halide or phosphoryl halide; even more preferably thionyl chloride.

The amount of the halogenating agent to be used is 1 to 5 mol, preferably 1 to 2 mol, per mol of the compound I.

Suitable bases include, for example, amines (e.g., pyridine, triethylamine, etc.).

Suitable solvents include, for example, hydrocarbons (e.g. toluene, benzene, etc.), halogenated hydrocarbons (e.g., dichloromethane, chloroform, 1,2-dichloroethane, chlorobenzene, etc.), ethers (e.g., diethyl ether, THF, dioxane, etc.). These organic solvents can be used alone or as mixture thereof.

Suitable phase-transfer catalysts include, for example, quaternary ammonium salts [e.g., tetraalkylammonium halides (e.g., tetrabutylammonium chloride, tetrabutylammonium bromide, etc.), -tetraalkylammonium hydrosulfates (e.g., tetrabutylammonium hydrosulfate, etc.),], amines (e.g., tris(3,6-dioxaheptyl)amine, etc.). The amount of the phase-transfer catalyst to be used is 0.01 to 1 mol, preferably 0.05 to 0.5 mol, per mol of the compound I.

The halogenation reaction is normally carried out at temperatures of from −20° C. to 150° C., preferably from 0° C. to 100° C., and the reaction time is generally between 0.5 and 2 hours.

The conversion into compounds IV, wherein LG is an optionally substituted alkylsulfonyloxy group or an optionally substituted arylsulfonyloxy group, can be carried out by reacting the compound I with e.g. an optionally substituted alkylsulfonyl halide (e.g. methanesulfonyl chloride, trifluoromethanesulfonyl chloride, etc.) or an optionally substituted arylsulfonyl halide (e.g. p-toluenesulfonyl chloride, benzenesulfonyl chloride, 4-bromophenylsulfonyl chloride, etc.), etc. The amounts of these halide compounds to be used are 1 to 5 mol, preferably 1.0 to 1.5 mol, per mol of the compound I. Preferably, the optionally substituted alkylsulfonyl halide is $C_1$-$C_6$-alkylsulfonyl halide, wherein alkyl is unsubstituted or substituted by 1, 2, 3, 4 or 5 halogen substituents. Even more preferably the $C_1$-$C_6$-alkyl moiety in $C_1$-$C_6$-alkylsulfonyl halide is selected from methyl, trifluoromethyl, ethyl, propyl, 1-methyl-ethyl, butyl, 1-methylpropyl, 2-methylpropyl (isobutyl), 1,1-dimethylethyl, pentyl, 1-methylbutyl, 2-methyl-butyl, 3-methylbutyl, 2,2-dimethylpropyl, 1-ethylpropyl, 1,1-dimethylpropyl, 1,2-dimethyl-prop-yl, hexyl, 1-methylpentyl, 2-methyl-pentyl, 3-methylpentyl, 4-methyl-pentyl, 1,1-di-methyl-butyl, 1,2-dimethylbutyl, 1,3-dimeth-yl-butyl, 2,2-dimethylbutyl, 2,3-dimethylbutyl, 3,3-di-methylbutyl, 1-ethylbutyl, 2-ethylbutyl, 1,1,2-trimethylpropyl, 1,2,2-tri-methylpropyl, 1-ethyl-1-methylpropyl and 1-ethyl-2-methylpropyl; even more preferably, from methyl and trifluoromethyl. Preferably, the optionally substituted alkylsulfonyl halide is $C_1$-$C_6$-alkylsulfonyl halide, wherein the alkyl moiety is unsubstituted or one $CH_3$— group of said alkyl is substituted by 3 halogen substituents, more preferably the alkyl moiety is unsubstituted.

Preferably the optionally substituted arylsulfonyl halide is phenylsulfonyl halide, wherein phenyl is unsubstituted or is substituted by 1, 2, 3, 4 or 5 substituents selected from halogen, $C_1$-$C_6$-alkyl, $C_1$-$C_6$-haloalkyl, $C_1$-$C_6$-haloalkoxy and cyclopropyl. More preferably, said substituents of the phenyl moiety are selected from Cl, Br, $CH_3$, $CH_2CH_3$, $CF_3$, $OCF_3$, and $OCHF_2$; even more preferably phenyl is unsubstituted or is substituted by one substituent as defined above; and utmost preferably phenyl is unsubstituted or is substituted by one substituent as defined above in para-position.

When the arylsulfonyl halide or the alkylsulfonyl halide is used, this reaction can be carried out in an appropriate solvent in the presence of a base.

Suitable solvents and bases are selected from the organic solvents and bases used in the abovementioned reaction using a halogenating agent.

The reaction using an arylsulfonyloxy or alkylsulfonyloxy halide is normally carried out at temperatures of from −20° C. to 100° C., preferably from −20° C. to 60° C., and the reaction time is generally between 0.5 and 5 hours.

The compound IV thus obtained can be used in the next step as crude product, or after purifying it by conventional methods (e.g., chromatography, recrystallization, etc.).

The compound IV may be treated with a hydroxyl compound of formula V $$R^3\text{—OH} \qquad \qquad \text{V,}$$

wherein
$R^3$ is phenyl or a 3- to 10-membered saturated, partially unsaturated or aromatic mono- or bicyclic heterocyclyl wherein the ring member atoms of the heterocyclyl include besides carbon atoms 1, 2, 3 or 4 heteroatoms selected from the group of N, O and S;
wherein the cyclic groups $R^3$ may carry 1, 2, 3, 4 or up to the maximum possible number of identical or different groups $R^b$ which independently of one another are selected from:
$R^b$, which may be the same or different to any other $R^b$, is amino, halogen, hydroxyl, oxo, nitro, CN, carboxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-cycloalkenyl, $C_2$-$C_6$-alkenyloxy, $C_3$-$C_6$-alkynyloxy, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_4$-alkylamino, $C_1$-$C_4$-alkoxycarbonyl, $C_1$-$C_4$-alkylcarbonyloxy, phenyl, naphthyl or a 3- to 10-membered saturated, partially unsaturated or aromatic mono- or bicyclic heterocyclyl which, in addition to carbon atoms, contains one to four heteroatoms from the group consisting of N, O and S as ring members; and wherein the aforementioned phenyl and heterocyclyl groups $R^b$ are attached via a direct bond, an oxygen or sulfur atom, and
two radicals $R^b$ that are bound to adjacent ring member atoms of the cyclic group $R^3$ may form together with said ring member atoms a fused 5-, 6- or 7-membered saturated, partially unsaturated or aromatic cycle, which may be a carbocycle or heterocycle, wherein the ring member atoms of the heterocycle include besides carbon atoms 1, 2, 3 or 4 heteroatoms selected from the group of N, O and S,
and
where the aliphatic or cyclic groups $R^b$ for their part may carry 1, 2, 3 or up to the maximum possible number of identical or different groups $R^c$:
$R^c$, which may be the same or different to any other $R^c$, is halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy, $C_1$-$C_4$-haloalkoxy, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkoxyimino-, $C_2$-$C_6$-alkenyloxyimino-, $C_2$-$C_6$-alkynyloxyimino-, $C_2$-$C_6$-haloalkenyloxyimino-, $C_3$-$C_6$-cycloalkyl, $C_3$-$C_6$-cycloalkenyl, phenyl or a 5-membered saturated, partially unsaturated or aromatic heterocyclyl which, in addition to carbon atoms, contains one to three heteroatoms from the group consisting of N, O and S as ring members;
wherein the aforementioned cyclic groups $R^c$ are attached via a direct bond, an oxygen or sulfur atom, and where the aliphatic or cyclic groups $R^c$ for their part may carry 1, 2, 3 or up to the maximum possible number of identical or different groups $R^d$:
$R^d$, which may be the same or different to any other $R^d$, is halogen, $C_1$-$C_4$-alkyl or $C_1$-$C_4$-haloalkyl;
or
$R^3$ is —$CR^A$=N—O—$R^B$, wherein
$R^A$ is amino, hydroxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-cycloalkenyl, $C_2$-$C_6$-alkenyloxy, $C_3$-$C_6$-alkynyloxy, $C_1$-$C_4$-alkoxyimino-$C_1$-$C_4$-alkyl, $C_1$-$C_4$-alkylamino, $C_1$-$C_4$-alkoxycarbonyl, $C_1$-$C_4$-alkylcarbonyloxy, phenyl, phenyl-$C_1$-$C_4$-alkyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members; and wherein the aforementioned cyclic $R^A$ are attached via a direct bond, an oxygen or sulfur atom;
$R^B$ is $C_1$-$C_4$-alkyl, $C_2$-$C_4$-alkenyl, $C_2$-$C_4$-alkynyl, $C_1$-$C_4$-haloalkyl, $C_3$-$C_6$-cycloalkyl, $C_3$-$C_6$-cycloalkenyl, $C_1$-$C_4$-alkoxyimino-$C_1$-$C_4$-alkyl, $C_1$-$C_4$-alkoxycarbonyl, phenyl, phenyl-$C_1$-$C_4$-alkyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members; where the aliphatic or cyclic groups $R^A$ and/or $R^B$ for their part may carry 1, 2, 3 or up to the maximum possible number of identical or different groups $R^e$:
$R^e$, which may be the same or different to any other $R^e$, is halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy or $C_1$-$C_4$-haloalkoxy;

to yield a (Z,2E)-5-cyclyloxy-2-methoxyimino-N-methyl-pent-3-enamide of formula VI wherein Y, R and $R^3$ are as defined above.

This reaction can be carried out in analogy to methods described earlier in WO 1996/07635; Nanjing Nongye Daxue Xuebao, 35(2), 141-145; 2012; and Chinese J. Chemistry, 27(10), 2055-2060; 2009.

Generally, the reaction is carried out at temperatures of from 23° C. to 140° C., preferably from 40° C. to 120° C., in an inert organic solvent in presence of a base or/and a catalyst (cf. NaF, KF, LiF, NaBr, KBr, LiBr, NaI, KI, LiI, Ionix liquid, imidazolium catalysts).

Suitable organic solvents include, for example, ketones (e.g., acetone, ethyl methyl ketone, nitriles (e.g., acetonitrile and propionitrile), ethers (e.g., dioxane and THF), DMF, hydrocarbons (e.g., toluene and o-, m- and p-xylene), and DMSO. These organic solvents can be used alone or as mixtures thereof.

Suitable bases are, in general, inorganic compounds such as alkali metal and alkaline earth metal oxides such as lithium oxide, sodium oxide, potassium oxide and calcium oxide; alkaline metal hydroxides (e.g., sodium hydroxide, potassium hydroxide); alkali metal and alkaline earth metal phosphates such as lithium phosphate, sodium phosphate, potassium phosphate and calcium phosphate; alkali metal and alkaline earth metal hydrides such as lithium hydride, sodium hydride, potassium hydride and calcium hydride; alkali metal and alkaline earth metal carbonates such as lithium carbonate, potassium carbonate, calcium carbonate, caesium carbonate and sodium hydrogen carbonate; Particular preference is given to lithium carbonate, potassium carbonate, calcium carbonate, caesium carbonate and sodium hydrogen carbonate.

The bases are generally employed in equimolar amounts, in excess or, if appropriate, as solvent. The amount of base is typically 1.1 to 5.0 molar equivalents relative to 1 mole of compounds V.

The starting materials, are generally reacted with one another in equimolar amounts. In terms of yields, it may be advantageous to employ an excess of compound V, based on 1.1 to 2.5 equivalents, preferred 1.1 to 1.5 equivalents relative to 1 mole of compound IV.

If necessary, this reaction may be carried out in the presence of a phase-transfer catalyst or metal halide. The phase-transfer catalysts include, for example, quaternary ammonium salts [e.g. tetraalkylammonium halides (e.g. tetrabutylammonium chloride, tetrabutylammonium bromide, etc.), tetraalkylammonium hydrosulfates (e.g. tetrabutylammonium hydrosulfate, etc.), etc.], amines (e.g. tris(3,6-dioxaheptyl)amine, etc.), etc. The amount of the phase-transfer catalyst to be used is 0.01 to 1 mol, preferably 0.05 to 0.5 mol, per mol of the compound IV. The metal halides include, for example, NaF, KF, LiF, NaBr, KBr, LiBr, NaI, KI, LiI, etc. The amount of the metal halide to be used is 0.01 to 5 mol, preferably 0.1 to 2 mol, per mol of the compound IV.

Compounds IV, wherein Y is hydrogen, may be obtained from corresponding compounds IV, wherein Y is not hydrogen, by various routes in analogy to prior art processes known (e.g. Tetrahedron Letters, 30 (4), 451-4; 1989; Synthesis, (20), 3129-34; 2007; European Journal of Organic Chemistry, (30), 5042-45 (2008); Journal of Organometallic Chemistry, 696 (23), 3643-48 (2011).

The compounds V are known from the literature or are commercially available or they can be prepared for example in analogy to methods described in WO 2013/092224. Educt and intermediate compounds such as compounds I, compounds II and compounds IV are not known.

Therefore, according to a second aspect, the invention provides compounds of formula I

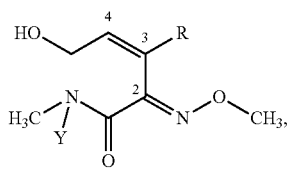

wherein
Y is hydrogen, $C_1$-$C_4$-alkoxy, $C_2$-$C_4$-alkenyl or benzyl;
R is $C_1$-$C_4$-alkyl, $C_1$-$C_4$-haloalkyl, $C_3$-$C_6$-cycloalkyl or $C_3$-$C_6$-cycloalkyl-$C_1$-$C_4$-alkyl; and wherein the —$CH_2$—OH group and the —C(=NOCH$_3$)C(=O)NYCH$_3$ group are on the same side of the C=C double bond between the carbon atoms depicted with the numbers 3 and 4 (Z-configuration), and
wherein the —OCH$_3$ group and the —C(=O)NYCH$_3$ group are on the opposite side of the C=N double bond between the carbon atom depicted with number 2 and the neighbouring nitrogen atom (E-configuration).

According to a third aspect, the invention provides compounds of formula II

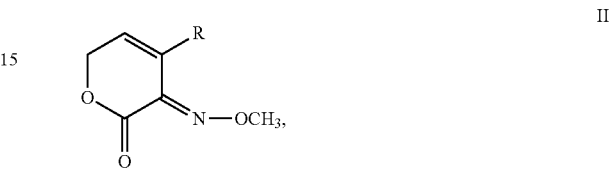

wherein
R is $C_1$-$C_4$-alkyl, $C_1$-$C_4$-haloalkyl, $C_3$-$C_6$-cycloalkyl or $C_3$-$C_6$-cycloalkyl-$C_1$-$C_4$-alkyl.

Therefore, according to a fourth aspect, the invention provides compounds of formula IV

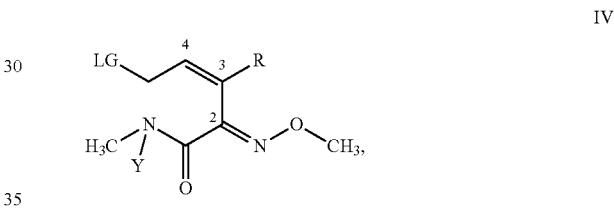

wherein
LG is a leaving group selected from halogen, optionally substituted alkylsulfonyloxy and optionally substituted arylsulfonyloxy
Y is hydrogen, $C_1$-$C_4$-alkoxy, $C_2$-$C_4$-alkenyl or benzyl;
R is $C_1$-$C_4$-alkyl, $C_1$-$C_4$-haloalkyl, $C_3$-$C_6$-cycloalkyl or $C_3$-$C_6$-cycloalkyl-$C_1$-$C_4$-alkyl; and
wherein the —$CH_2$—OH group and the —C(=NOCH$_3$)C(=O)NYCH$_3$ group are on the same side of the C=C double bond between the carbon atoms depicted with the numbers 3 and 4 (Z-configuration), and
wherein the —OCH$_3$ group and the —C(=O)NYCH$_3$ group are on the opposite side of the C=N double bond between the carbon atom depicted with number 2 and the neighbouring nitrogen atom (E-configuration).

LG is preferably selected from halogen, $C_1$-$C_6$-alkylsulfonyloxy, wherein alkyl is unsubstituted or substituted by 1, 2, 3, 4 or 5 halogen substituents, and phenylsulfonyloxy, wherein phenyl is unsubstituted or is substituted by 1, 2, 3, 4 or 5 substituents selected from halogen, $C_1$-$C_6$-alkyl, $C_1$-$C_6$-haloalkyl, $C_1$-$C_6$-haloalkoxy and cyclopropyl. The halogen represented by LG include, for example, chlorine, bromine and iodine, preferably chlorine and bromine.

The optionally substituted alkylsulfonyloxy in LG is preferably $C_1$-$C_6$-alkylsulfonyloxy, wherein alkyl is unsubstituted or substituted by 1, 2, 3, 4 or 5 halogen substituents. Even more preferably the $C_1$-$C_6$-alkyl moiety in $C_1$-$C_6$-alkylsulfonyloxy is selected from methyl, ethyl, propyl, 1-methyl-ethyl, butyl, 1-methylpropyl, 2-methylpropyl (isobutyl), 1,1-dimethylethyl, pentyl, 1-methylbutyl, 2-methyl-butyl, 3-methylbutyl, 2,2-dimethylpropyl, 1-ethylpropyl, 1,1-dimethylpropyl, 1,2-dimethyl-prop-yl, hexyl, 1-methylpentyl, 2-methylpentyl, 3-methyl pentyl, 4-methyl-pentyl, 1,1-di-methyl-butyl, 1,2-dimethylbutyl, 1,3-dimethyl-butyl, 2,2-dimethylbutyl, 2,3-di-methylbutyl, 3,3-dimethylbutyl, 1-ethylbutyl, 2-ethylbutyl, 1,1,2-trimethylpropyl, 1,2,2-tri-methylpropyl, 1-ethyl-1-methylpropyl and 1-ethyl-2-methylpropyl. More preferably, the optionally substituted alkylsulfonyloxy groups are selected from methanesulfonyloxy, trifluoromethanesulfonyl-oxy; in particular methanesulfonyloxy. Preferably, the optionally substituted alkylsulfonyloxy is $C_1$-$C_6$-alkylsulfonyloxy, wherein the alkyl moiety is unsubstituted or one $CH_3$— group of said alkyl is substituted by 3 halogen substituents, more preferably the alkyl moiety is unsubstituted.

The optionally substituted arylsulfonyloxy in LG is preferably selected from phenylsulfonyloxy, wherein phenyl is unsubstituted or is substituted by 1, 2, 3, 4 or 5 substituents selected from halogen, $C_1$-$C_6$-alkyl, $C_1$-$C_6$-halo-alkyl, $C_1$-$C_6$-haloalkoxy and cyclopropyl; more preferably said substituents of the phenyl moiety are selected from Cl, Br, $CH_3$, $CH_2CH_3$, $CF_3$, $OCF_3$, and $OCHF_2$; even more preferably phenyl is unsubstituted or is substituted by one substituent as defined above; and utmost preferably phenyl is unsubstituted or is substituted by one substituent as defined above in para-position. The optionally substituted arylsulfonyloxy groups represented by LG include, for example, p-toluenesulfonyloxy, 4-bromophenylsulfonyloxy, benzenesulfonyloxy, etc. preferably, p-toluenesulfonyloxy and benzenesulfonyloxy.

The compounds II can be prepared, for example, from 3-methoxyimino-tetrahydropyran-2-one compounds VII by a dehydrohalogenation, i.e. dehydrobromination. Treatment of the halogenated oximeter VIII directly with a base resulting in removal of H-Hal to furnish lacton II as an E,Z-isomer mixture:

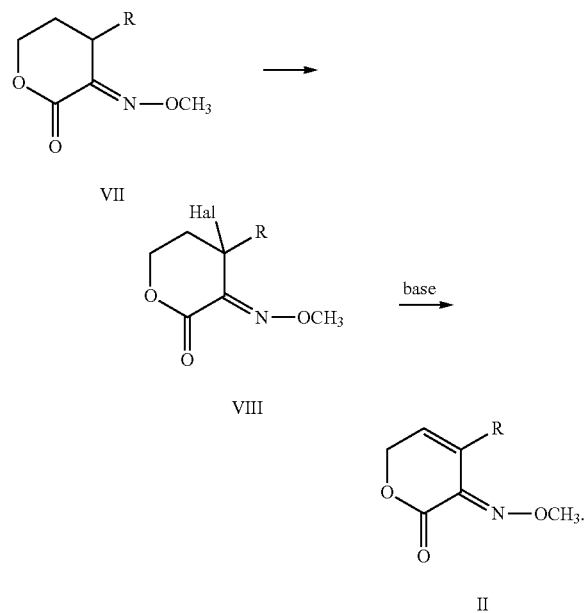

In the first step, a radical halogenation of compound VII is effected using a free radical halogenating agent in a suitable organic solvent, preferably in the presence of light or a radical initiator.

Suitable free radical halogenating agents are, for example, N-bromosuccinimide (NBS), N-chlorosuccinimide (NCS), $SO_2Cl_2$, 1,3-dibromo-5,5-dimethylhydantoin (DBDMH) and bromine. Particularly preferred are NBS and DBDMH.

Suitable radical initiators are, for example, di-tert-butyl peroxide (t-BuOOt-Bu), dibenzoyl peroxide (DBPO) or azobisisobutyronitrile (AIBN).

Generally, the reaction is carried out at temperatures of from 40° C. to 80° C., preferably from 40° C. to 60° C. in an inert organic solvent and in the presence of a radical initiator.

Suitable organic solvents are halogenated hydrocarbons such as chlorobenzene, dichlorobenzene and $CCl_4$; nitriles such as acetonitrile and propionitrile; acetic acid ethyl ester (ethyl acetate) and acetic acid methyl ester(methyl acetate) can be used to good effect. Particularly preferred are chlorobenzene, $CCl_4$, ethylacetate and methyl acetate.

The reaction mixture obtained can be worked up and the compound VIII can be isolated in a customary manner, e.g. by an aqueous, extractive workup, by removing the solvent, e.g. under reduced pressure, or by a combination of these measures. Further purification can be effected, for example, by crystallization, distillation or by chromatography.

Optionally, the reaction mixture can be used without further workup for the second step.

In the second step, compound VIII or the reaction mixture of the first step is treated with a base to obtain compound II.

Generally, this reaction step is carried out at temperatures of from 20° C. to 120° C., preferably from 40° C. to 70° C., in an inert organic solvent in presence of a base or/and a catalyst (cf. NaF, KF, LiF, NaBr, KBr, LiBr, NaI, KI, LiI, LiCl, Ionix liquid, imidazolium catalysts).

Suitable solvents are ethers such as dioxane, anisole and THF; nitriles such as acetonitrile and propionitrile; ketones, such as acetone, methyl ethyl ketone, diethyl ketone and tert-butyl methyl ketone; alcohols such as ethanol, n-propanol, isopropanol, n-butanol and tert-butanol; and also DMSO, DMF, dimethyl acetamide, NMP, NEP and acetic acid ethyl ester. Aprotic solvents including ethers like THF, esters like ethyl acetate, nitriles like acetonitrile, amides like DMF and NMP and sulfoxides like DMSO are being especially preferred. It is also possible to use mixtures of the solvents mentioned. Preferably, mixtures of esters and ethers or amides are used such as mixtures of ethyl acetate and THF or ethyl acetate and DMF.

Suitable bases are, in general, inorganic compounds such as alkali metal and alkaline earth metal oxides such as lithium oxide, sodium oxide, potassium oxide and calcium oxide; alkali metal and alkaline earth metal phosphates such as lithium phosphate, sodium phosphate, potassium phosphate and calcium phosphate; alkali metal and alkaline earth metal hydrides such as lithium hydride, sodium hydride, potassium hydride and calcium hydride; alkali metal and alkaline earth metal carbonates such as lithium carbonate, potassium carbonate, calcium carbonate, caesium carbonate and sodium hydrogen carbonate; moreover organic bases, e.g. tertiary amines such as trimethylamine, triethylamine, tributylamine, diisopropylethylamine and NMP, pyridine, substituted pyridines such as collidine, lutidine and 4 dimethylaminopyridine, and also bicyclic amines.

Particular preference is given to lithium carbonate, potassium carbonate, calcium carbonate, caesium carbonate and sodium hydrogen carbonate.

The bases are generally employed in equimolar amounts, in excess or, if appropriate, as solvent. The amount of base is typically 1.1 to 10.0 molar equivalents relative to 1 mole of compounds VII and likewise compounds VII as educts of the first step.

Thus, the invention also relates to a process for preparing 5-methoxyimino-2H-pyran-6-one compounds of formula II

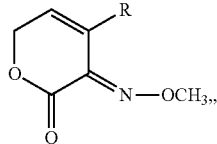

wherein

R is $C_1$-$C_4$-alkyl, $C_1$-$C_4$-haloalkyl, $C_3$-$C_6$-cycloalkyl or $C_3$-$C_6$-cycloalkyl-$C_1$-$C_4$-alkyl.

the process comprising:

a) reacting a compound of formula VII

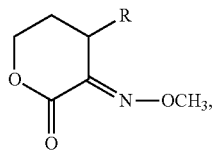

wherein R is defined as above;

with a free-radical halogenating agent in an organic solvent to obtain intermediate compounds VIII

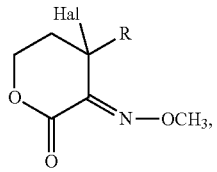

wherein Hal is halogen and R is defined as above;
and b) after the first reaction step, treating the reaction mixture of step a) or compounds VIII with at least one base to obtain compounds II.

Compounds VII can be prepared, e.g. from tetrahydropyran-2-one compounds IX according to the following scheme by α-oximation with a nitrite such as Alkyl-O—N=O, preferably in the presence of a base and followed by alkylation using methyl halogenides or dimethyl sulfate.

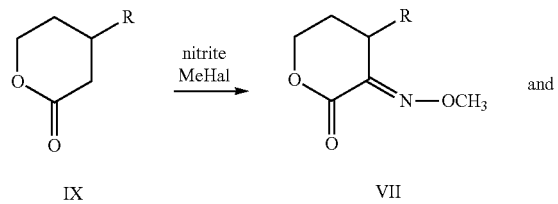

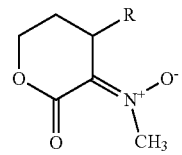

Suitable solvents are aliphatic hydrocarbons; aromatic hydrocarbons such as toluene, o-, m- and p-xylene; halogenated hydrocarbons chlorobenzene, dichlorobenzene; ethers such as dioxane, anisole and THF, MtBE; alcohols such as methanol, ethanol, n-propanol, isopropanol, n-butanol and tert-butanol; and also toluene, DMSO, DMF, dimethyl acetamide, NMP, NEP. Solvents like toluene, THF, MtBE, DMF, Methanol, Ethanol and NMP are being especially preferred. It is also possible to use mixtures of the solvents mentioned.

Suitable nitrites are, in general methyl nitrite, ethyl nitrite, n-propyl nitrite, tert-butyl nitrite, 3-methylbutyl nitrite (amyl nitrite), isoamyl nitrite, isopentyl nitrite, n-butyl nitrite, cyclohexyl nitrite, n-hexyl nitrite, isobutyl nitrite and isopropyl nitrite. Particular preference is given to tert-butyl nitrite, amyl nitrite, isoamyl nitrite, isopentyl nitrite, n-butyl nitrite and isobutyl nitrite. The alkyl nitrites are generally employed in equimolar amounts or in excess, if appropriate. The amount of alkyl nitrites is typically 1.1 to 5.0 molar equivalents preferred 1.1 to 3 equivalents relative to 1 mole of compounds IX.

Suitable bases are, in general, alkali metal amides such as lithium amide, sodium amide and potassium amide; alkali metal and alkaline earth metal hydrides lithium hydride, sodium hydride, potassium hydride and calcium hydride; alkali metal and alkaline earth metal carbonates such as lithium carbonate, potassium carbonate and calcium carbonate, caesium carbonate; sodium methylate, potassium methylate, sodium tert-butoxide, potassium tert-butoxide, sodium iso-propoxide, potassium iso-propoxide, lithium diisopropylamide (LDA) and lithium tetramethylpiperidide (LiTMP). Particular preference is given to sodium methylate, potassium methylate, sodium tert-butoxide and potassium tert-butoxide.

The bases are generally employed in equimolar amounts, in excess or, if appropriate, as solvent. The amount of base is typically 1.1 to 5.0 molar equivalents preferred 1.1 to 2.5 equivalents relative to 1 mole of compounds IX.

Suitable alkylating agents MeHal are iodomethane, chloromethane, bromomethane or dimethyl sulfate, preferably bromomethane, chloromethane or dimethyl sulfate.

The α-oximation usually provides a mixture of two geometric isomers (Z and E) of the corresponding oximes VII.

The alkylation with methyl halogenide or dimethyl sulfate is not completely regioselective and about 10% of the N-alkylated byproduct (nitrone) was formed.

Here, it was found that, the undesired N-alkylated byproduct (nitrone) VIIb could avoided in the α-oximation reaction of compounds IX with a nitrite such as alkyl nitrite (Alkyl-O—N=O), by using $Ag_2O$ as base preferably in the presence of an unpolar solvent.

Suitable unpolar solvents are halogenated aliphatic hydrocarbons such as methylene chloride, carbon tetrachloride, 1,1-dichloroethane, 1,2-dichloroethane, 1,2-dichloropropane; aliphatic hydrocarbons such as n-pentane, n-hexane, n-heptane, cyclohexane; aromatic hydrocarbons such as toluene, o-, m- and p-xylene; halogenated hydrocarbons such as chlorobenzene, dichlorobenzene. Solvents like methylene chloride, 1,1-dichloroethane, 1,2-dichloroethane, chlorobenzene, toluene, n-hexane and n-heptane are being especially preferred. It is also possible to use mixtures of the solvents mentioned.

Compounds IX are known from the literature or are commercially available or they can be prepared for example in analogy to methods described in Advanced Synthesis 8, Catalysis, 354(18), 3405-3408; 2012 and Tetrahedr, Lett. 43(7), 1189-1191, 2002.

It was further found that, the undesired N-alkylated byproduct (nitrone) VIIb could be transformed to the desired O-alkylated oxime ether VII by treatment with methoxyamine or methoxyamine halogenide preferably methoxyamine hydrochloride in a suitable organic solvent, if necessary, in the presence of an mineral acid (inorganic acid).

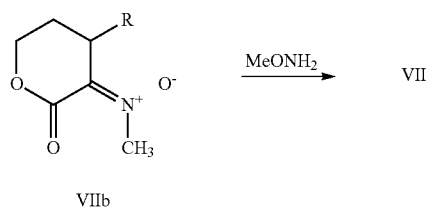

VIIb

Suitable solvents are ethers such as dioxane, anisole and THF; nitriles such as acetonitrile and propionitrile; sulfoxides like DMSO; and amides like DMF, dimethyl acetamide, NMP and NEP. Aprotic solvents including ethers like THF, nitriles like acetonitrile, amides like DMF, NMP and sulfoxides like DMSO are being especially preferred.

The reaction is typically conducted at temperature from about 20° C. to about 140° C. and preferably from about 20° C. to 80° C.

In a typical reaction, methoxyamine or methoxyamine hydrochloride is generally employed in equimolar amount or in excess, e.g. a 1 to 5 molar equivalents relative to 1 mole of compounds VIIb. It is often convenient to use an excess of the methoxyamine omethoxyamine hydrochloride typically a 1.1 to 3.0 molar equivalents and preferably 1.1 to 2.0 molar equivalents relative to 1 mole of compounds VIIb.

Suitable mineral acids include hydrochloric, sulfuric and phosphoric acids with hydrochloric acid being preferred. The mineral acids are usually used as aqueous solutions. Typically 0.01 to 0.1 molar equivalent of mineral acid relative to 1 mole of compounds VIIb is required.

The invention is illustrated by the following examples:

1. (3E,Z)-3-methoxyimino-4-methyl-tetrahydropyran-2-one

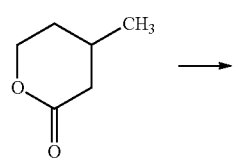

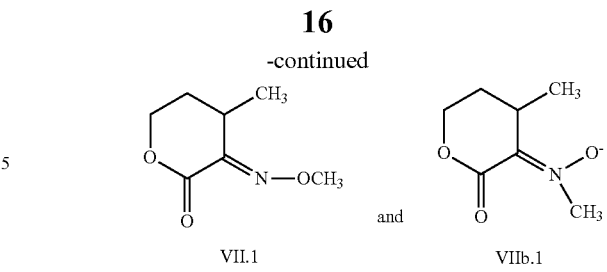

VII.1 and VIIb.1

A solution of 500.0 g (4.3 mol) β-methyl-δ-valerolactone in 1500 ml toluene was treated with 1084.29 g (10.51 mol) tert-butylnitrite. To this mixture was added 737.32 g (6.57 mmol) potassium tert-butoxide (KOtBu) carefully in small portions over 60 min with stirring at 35° C. After 2 h at 40° C. iodomethane (1865.3 g, 13.11 mol) was added dropwise. The resulting mixture was stirred at about 23° C. overnight and quenched with cold 10% aqueous $NaH_2PO_4$ (10 L) and 74 ml of 12 N HCl (pH 5), then extracted with MTBE. The extracts were washed with 10% aqueous $NaH_2PO_4$, dried over anhydrous $Na_2SO_4$ and evaporated under vacuum. The residue (495 g) was chromatographed on silica gel using a gradient of 1:1 cyclohexane-MTBE to obtain 237 g (34.5%) product as an E,Z isomer mixture and 56.4 g (8.2%) of the N-alkylated nitrone.

VII.1: $^1$H-NMR (CDCl$_3$): δ=1.2 (d); 1.7 (m); 2.2 (m); 3.3 (m); 4.1 (s); 4.23 (m); 4.5 (m);

VIIb.1: $^1$H-NMR (CDCl$_3$): δ=1.2 (d); 1.7 (m); 2.2 (m); 3.4 (m); 4.2 (s); 4.23 (m); 4.4 (m).

1.1 (3E,Z)-3-methoxyimino-4-methyl-tetrahydropyran-2-one from nitrone

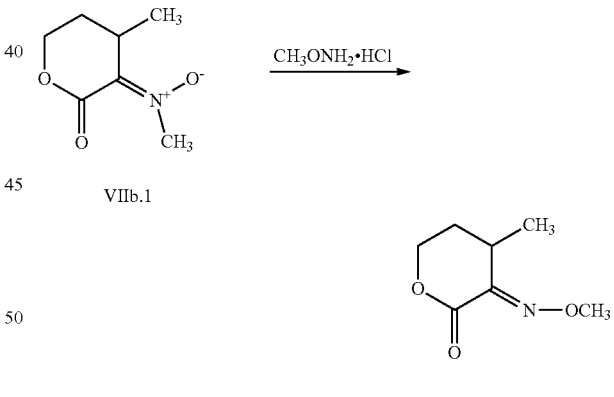

A solution of 56.35 g (358 mmol) nitrone (see byproduct of Ex. 1) in 400 ml DMF was treated with 59.89 g (717 mmol) CH$_3$ONH$_2$.HCl and the resulting mixture was stirred at 60° C. for 3 h, quenched with cold 10% aqueous NaH$_2$PO$_4$ and extracted with MTBE. The extracts were washed with saturated brine, dried over anhydrous Na$_2$SO$_4$ and evaporated under vacuum. The residue was chromatographed on silica gel using a gradient of 1:1 cyclohexane-MTBE to obtain 45 g (80%) product.

VII.1: $^1$H-NMR (CDCl$_3$): δ=1.2 (d); 1.7 (m); 2.2 (m); 3.3 (m); 4.1 (s); 4.23 (m); 4.5 (m).

2. (3E,Z)-4-bromo-3-methoxyimino-4-methyl-tetrahydropyran-2-one

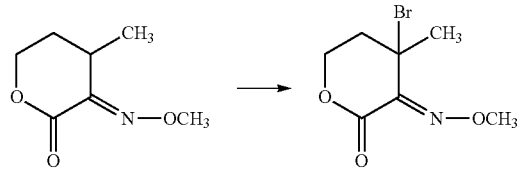

In 500 ml CCl$_4$ 5.64 g (35.6 mmol) (3E,Z)-3-methoxyimino-4-methyl-tetrahydropyran-2-one (see Ex. 1) and 6.98 g (39.1 mmol) NBS were dissolved and a small amount of dibenzoyl peroxide was added and the mixture was refluxed for 1.5 h. The mixture was allowed to cool to about 23° C. and was filtered through a sintered glass plug of silica gel. The filtrate was evaporated in vacuo and the residue (8.72 g) was chromatographed on silica gel using cyclohexane-MTBE.

Yield 6.72 g (79.8%) oil as a 82:18 E,Z-isomer mixture.
$^1$H-NMR (CDCl$_3$): δ=2.1 (s); 2.4 (m); 4.22 (s); 4.4 (m); 4.78 (m).

3. (5E,Z)-5-methoxyimino-4-methyl-2H-pyran-6-one

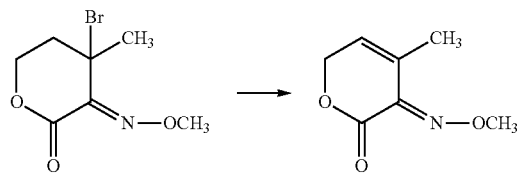

A solution of 0.5 g (2.1 mmol) (3E,Z)-4-bromo-3-methoxyimino-4-methyl-tetrahydropyran-2-one (see Ex. 2) in 10 ml DMF was treated with 0.78 g (10 mmol) lithium carbonate and stirred for 2 h at 45° C. for and then at 60° C. until reaction completion was confirmed by HPLC analysis (approx. 1 h). The resulting mixture was partitioned between MTBE and 10% aqueous NaH$_2$PO$_4$ and of 12 N HCl (1.5 ml). The aqueous layer was extracted with MTBE and the combined organic layers were dried over anhydrous Na$_2$SO$_4$ to afford 0.26 g as an E,Z-isomer mixture.

(Z)-Isomer: $^1$H-NMR (CDCl$_3$): δ=1.97 (s); 4.13 (s); 4.97 (s); 6.00 (t).

(E)-Isomer: $^1$H-NMR (CDCl$_3$): δ=2.20 (s); 4.10 (s); 4.90 (s); 6.00 (t).

4. (Z,2E)-5-hydroxy-2-methoxyimino-N,3-dimethyl-pent-3-enamide

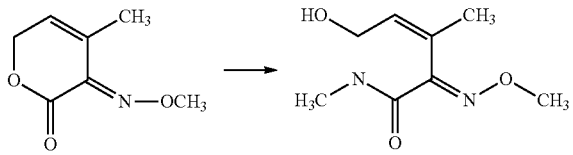

A solution of 2.55 g (16.4 mmol) (5E,Z)-5-methoxyimino-4-methyl-2H-pyran-6-one (see Ex. 3) in 20 ml THF was treated with 2.2 g (131 mmol) 40% aqueous methylamine and stirred at about 23° C. overnight. After removal of the solvents in vacuo the residue was chromatographed on silica gel using cyclohexane-MTBE. Yield 2.26 g (74%) as pure Z,2E-isomer. $^1$H-NMR (CDCl$_3$): δ=1.86 (s); 2.90 (d); 3.80 (d); 4.0 (s); 5.93 (t); 6.80 (broad).

5. (Z,2E)-5-hydroxy-2-methoxyimino-N,3-dimethyl-pent-3-enamide

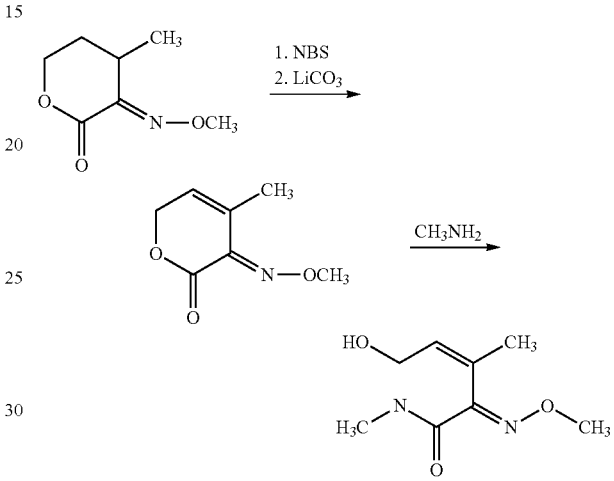

3.93 g (25 mmol) (3E,Z)-3-methoxyimino-4-methyl-tetrahydropyran-2-one (see Ex. 1) and 4.89 g (27.5 mmol) NBS were dissolved in 150 ml ethyl acetate, a small amount of dibenzoyl peroxide (0.81 g) was added and the mixture was refluxed at about 65° C. for 1.5 h. The mixture was allowed to cool to about 23° C. and 100 ml of DMF was added, treated with 11 g (150 mmol) LiCO$_3$ and stirred for 3 h at about 65° C. until reaction completion was confirmed by HPLC analysis. The mixture was cooled down to about 23° C., it was filtered and washed with ethyl acetate. The organic layer was washed three times with 30% solution of LiCl in water (3×100 ml). The LiCl phase was extracted twice with ethyl acetate and the combined organic layers were dried over anhydrous Na$_2$SO$_4$ and concentrated under vacuum at about 30° C. The residue (4.9 g) was diluted with 45 ml THF followed by 40% aqueous methylamine (30 ml) and the mixture stirred for 90 min at 50° C.

The reaction mixture was concentrated under vacuum to the volume of 25 ml, saturated with solid NaCl and extracted four times with ethyl acetate. The combined organic layers were dried over sodium sulfate, concentrated under vacuum and chromatographed on silica gel using ethyl acetate to obtain 2.1 g product as Z,2E-isomer (>95%) as an oil that crystallized upon standing.

$^1$H-NMR (CDCl$_3$): δ=1.86 (s); 2.90 (d); 3.80 (d); 4.0 (s); 5.93 (t); 6.80 (broad).

6. (Z,2E)-5-chloro-2-methoxyimino-N,3-dimethyl-pent-3-enamide

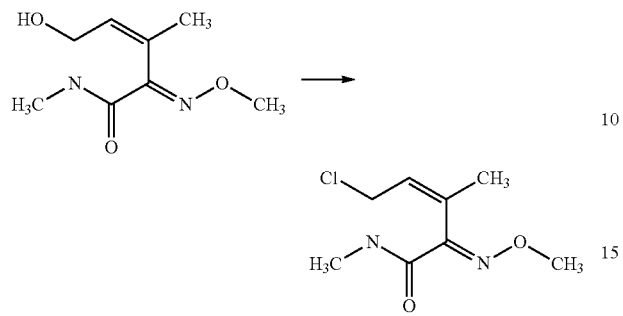

2.25 g (12 mmol) (Z,2E)-5-hydroxy-2-methoxyimino-N,3-dimethyl-pent-3-enamide (see Ex. 5) have been dissolved in 50 ml dichloromethane. 1.83 g (18.1 mmol) triethylamine and 3.45 g (28.9 mmol) thionyl chloride dissolved in dichloromethane have been added with stirring at room temperature. After stirring overnight at about 23° C. 50% of the solvents have been removed in vacuo, the residue was diluted with MTBE before careful addition of aqueous NaHCO$_3$. The precipitated salt was collected and washed with MTBE. The aqueous layer was extracted with MTBE and the combined organic layers were washed with saturated NaHCO$_3$ and water and dried over anhydrous Na$_2$SO$_4$. Yield 2.47 g (85.3%), mp. 62° C.

$^1$H-NMR (CDCl$_3$): δ=1.93 (s); 2.92 (d); 3.8 (d); 4.0 (s); 5.80 (t); 6.7 (broad).

7. (Z,2E)-5-[1-(4-chlorophenyl)pyrazol-3-yl]oxy-2-methoxyimino-N,3-dimethyl-pent-3-enamide

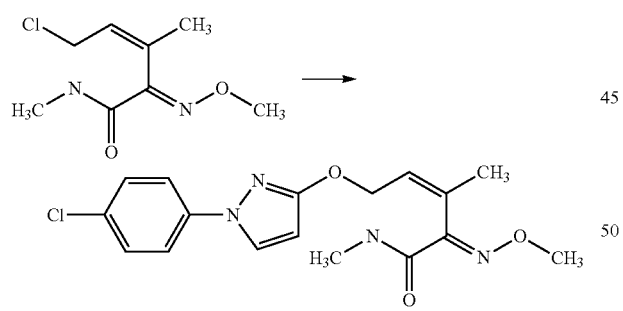

480 mg (2.4 mmol) (Z,2E)-5-chloro-2-methoxyimino-N,3-dimethyl-pent-3-enamide (see Ex. 6) and 500 mg (2.44 mmol) 1-(4-chlorophenyl)pyrazol-3-ol have been dissolved in 10 ml DMF. 680 mg (4.8 mmol) K$_2$CO$_3$ and 20 mg KI have been added with stirring for 2 h at 60° C. and then overnight at about 23° C. The reaction mixture was diluted with water, extracted with MTBE, the combined extracts were washed with water once and dried over anhydrous Na$_2$SO$_4$. After removal of the solvents in vacuo and the residue (0.71 g) chromatographed on silica gel using cyclohexane-MTBE to afford a yellow oil that crystallized upon standing: 460 mg (51.9%). mp: 126-128° C.

8. Comparative example for preparation of 5-[1-(4-chlorophenyl)pyrazol-3-yl]oxy-2-meth-oxyimino-N,3-dimethyl-pent-3-enamide (Compound IV from Ex. 7) in analogy to method described in WO 2013/092224

8a. 2-[1-(4-chlorophenyl)pyrazol-3-yl]oxyacetaldehyde

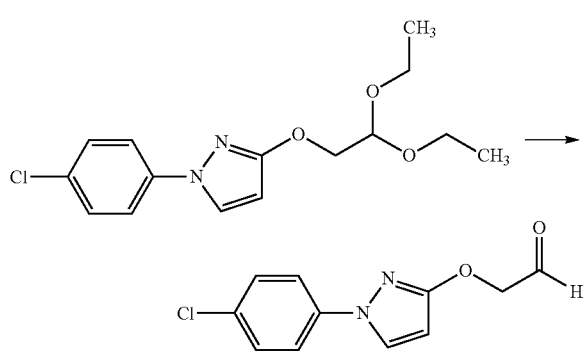

4.86 g (15.63 mmol) 1-(4-chlorophenyl)-3-(2,2-diethoxy)pyrazol was treated with 150 ml 1 N hydrochloric acid solution in diethyl ether and stirred at about 23° C. overnight until reaction completion was confirmed by HPLC analysis. The reaction mixture was concentrated under vacuum, diethyl ether was added, washed with NaHCO$_3$ solution and brine, dried over anhydrous Na$_2$SO$_4$ and concentrated under vacuum at about 29° C. to yield the title compound (3.8 g) that was used without further purification.

8b. Methyl-5-[-(1-(4-chlorophenyl)pyrazol-3-yl]oxy-2methoxyimino-3-methyl-pent-3-enoate

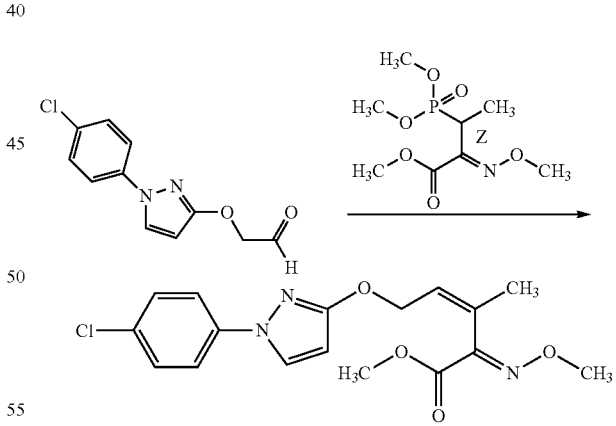

To 3.8 g 2-[1-(4-chlorophenyl)pyrazol-3-yl]oxyacetaldehyde in 90 ml THF 3.16 g (12.5 mmol) methyl (2Z)-3-dimethoxyphosphoryl-2-methoxyimino-butenoate (U.S. Pat. No. 5,346,898) was added, followed by 1.6 g (15 mmol) potassium tert-butylate in 30 ml THF. The reaction mixture was stirred at about 23° C. overnight and then concentrated. The residue was dissolved in MTBE, washed three times with water, dried over anhydrous Na$_2$SO$_4$, concentrated under vacuum and chromatographed on silica gel using a gradient of 3:1 heptane-MTBE to obtain 0.86 g product.

8c. 5-[1-(4-chlorophenyl)pyrazol-3-yl]oxy-2-methoxyimino-N,3-dimethyl-pent-3-enamide

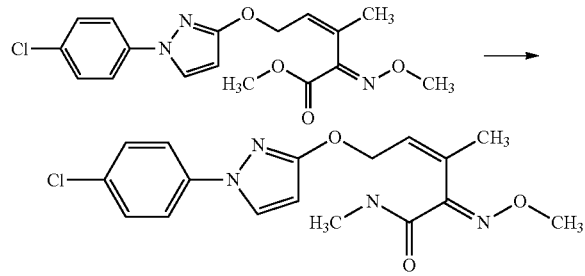

To 0.86 g methyl 5-[1-(1-(4-chlorophenyl)pyrazol-3-yl]oxy-2methoxyimino-3-methyl-pent-3-enoate in 20 ml THF was added 9.1 g 30% methylamine in THF and stirred at 55° C. After 8 h additional 20 ml 30% methylamine in THF was added and this process repeated after 6 h. The reaction mixture was concentrated under vacuum. The residue was dissolved in 200 ml MTBE, washed twice with brine, dried over anhydrous $Na_2SO_4$ and concentrated under vacuum. The residue was chromatographed on silica gel using a gradient of 1:1 heptane-MTBE to obtain:

34 mg of the desired isomer (Z,2E)-5-[1-(4-chlorophenyl)pyrazol-3-yl]oxy-2-methoxyimino-N,3-dimethyl-pent-3-enamide $^1$H-NMR ($CDCl_3$): δ=1.98 (s); 2.68 (d); 3.98 (s); 4.92 (d); 5.9 (m, 2H); 5.9 (m); 6.9 (broad); 7.23 (s); 7.38 (m); 7.5 (m); 7.7 (s).

28 mg of the undesired isomer (E,2Z)-5-[1-(4-chlorophenyl)pyrazol-3-yl]oxy-2-methoxyimino-N,3-dimethyl-pent-3-enamide $^1$H-NMR ($CDCl_3$): δ=1.95 (s); 2.95 (d); 3.98 (s); 4.98 (d); 5.0 (d); 5.9 (m); 6.1 (m); 7.23 (s); 7.4 (m); 7.44 (m); 7.7 (s).

Thus, the comparative example 8 provided a stereoselectivity of 34 mg to 28 mg which corresponds to a ratio of about 1.2:1 (ratio of the desired (Z,2E)-isomer of versus the sum of the corresponding (E,2E)-, (E,2Z)- and (Z,2Z)-isomers).

The invention claimed is:
1. A process for preparing compounds of formula I

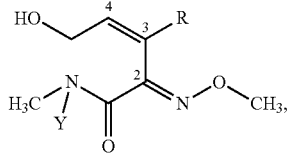

wherein
R is $C_1$-$C_4$-alkyl, $C_1$-$C_4$-haloalkyl, $C_3$-$C_6$-cycloalkyl or $C_3$-$C_6$-cycloalkyl-$C_1$-$C_4$-alkyl;
Y is hydrogen, $C_1$-$C_4$-alkoxy, $C_2$-$C_4$-alkenyl or benzyl; and
wherein the —$CH_2$—OH group and the —C(=$NOCH_3$)C(=O)NYCH$_3$ group are on the same side of the C=C double bond between the carbon atoms depicted with the numbers 3 and 4 (Z-configuration), and
wherein the —$OCH_3$ group and the —C(=O)NYCH$_3$ group are on the opposite side of the C=N double bond between the carbon atom depicted with number 2 and the neighbouring nitrogen atom (E-configuration);
the process comprising:
reacting a compound of formula II

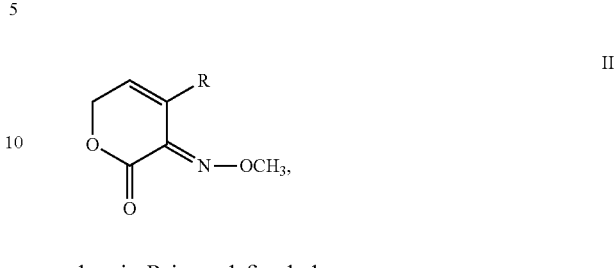

wherein R is as defined above;
with a compound of formula III

wherein Y is as defined above.

2. The process as claimed in claim 1, wherein a mixture of the E/Z-isomers of compounds of formula II is used, wherein said mixture comprises an E/Z-isomer ratio of from 0.1:1 to 10:1.

3. The process as claimed in claim 1, wherein R is $C_1$-$C_4$-alkyl or $C_1$-$C_4$-halogenalkyl.

4. The process as claimed in claim 3, wherein R is methyl of $CF_3$.

5. The process as claimed in claim 1, wherein Y is allyl (prop-2-enyl), benzyl, methoxy or hydrogen.

6. The process as claimed in claim 5, wherein Y is hydrogen.

7. The process as claimed in claim 1, additionally comprising treating the compound I with a halogenating agent, n $C_1$-$C_6$-alkylsulfonyloxy halide, wherein alkyl is unsubstituted or substituted by 1, 2, 3, 4 or 5 halogen substituents, or phenylsulfonyl halide, wherein phenyl is unsubstituted or is substituted by 1, 2, 3, 4 or 5 substituents selected from halogen, $C_1$-$C_6$-alkyl, $C_1$-$C_6$-haloalkyl, $C_1$-$C_6$-haloalkoxy and Cyclopropyl, to yield a compound of formula IV

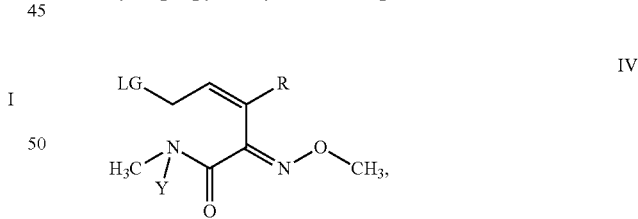

wherein
LG is a leaving group selected from
halogen,
$C_1$-$C_6$-alkylsulfonyloxy, wherein alkyl is unsubstituted or substituted by 1, 2, 3, 4 or 5 halogen substituents, and
phenylsulfonyloxy, wherein phenyl is unsubstituted or is substituted by 1, 2, 3, 4 or 5 substituents selected from halogen, $C_1$-$C_6$-alkyl, $C_1$-$C_6$-haloalkyl, $C_1$-$C_6$-haloalkoxy and cyclopropyl.

8. The process as claimed in claim 7, wherein LG is halogen and the halogenating agent is thionyl halide or phosphoryl halide.

9. The process as claimed in claim 7, additionally comprising treating the compound IV with a hydroxyl compound of formula V $$R^3\text{—OH} \qquad\qquad V,$$

wherein

R$^3$ is phenyl or a 3- to 10-membered saturated, partially unsaturated or aromatic mono- or bicyclic heterocyclyl wherein the ring member atoms of the heterocyclyl include besides carbon atoms 1, 2, 3 or 4 heteroatoms selected from the group of N, O and S;

wherein the cyclic groups R$^3$ may carry 1, 2, 3, 4 or up to the maximum possible number of identical or different groups R$^b$ which independently of one another are selected from:

R$^b$, which may be the same or different to any other R$^b$, is amino, halogen, hydroxyl, oxo, nitro, CN, carboxyl, C$_1$-C$_4$-alkyl, C$_2$-C$_4$-alkenyl, C$_2$-C$_4$-alkynyl, C$_1$-C$_4$-haloalkyl, C$_1$-C$_4$-alkoxy, C$_1$-C$_4$-haloalkoxy, C$_3$-C$_6$-cycloalkyl, C$_3$-C$_6$-cycloalkenyl, C$_2$-C$_6$-alkenyloxy, C$_3$-C$_6$-alkynyloxy, C$_1$-C$_6$-alkoxyimino-C$_1$-C$_4$-alkyl, C$_2$-C$_6$-alkenyloxyimino-C$_1$-C$_4$-alkyl, C$_2$-C$_6$-alkynyloxyimino-C$_1$-C$_4$-alkyl, C$_1$-C$_4$-alkylamino, C$_1$-C$_4$-alkoxycarbonyl, C$_1$-C$_4$-alkylcarbonyloxy, phenyl, naphthyl or a 3- to 10-membered saturated, partially unsaturated or aromatic mono- or bicyclic heterocyclyl which, in addition to carbon atoms, contains one to four heteroatoms from the group consisting of N, O and S as ring members; and wherein the aforementioned phenyl and heterocyclyl groups R$^b$ are attached via a direct bond, an oxygen or sulfur atom, and two radicals R$^b$ that are bound to adjacent ring member atoms of the cyclic group R$^3$ may form together with said ring member atoms a fused 5-, 6- or 7-membered saturated, partially unsaturated or aromatic cycle, which may be a carbocycle or heterocycle, wherein the ring member atoms of the heterocycle include besides carbon atoms 1, 2, 3 or 4 heteroatoms selected from the group of N, O and S, and where the aliphatic or cyclic groups R$^b$ for their part may carry 1, 2, 3 or up to the maximum possible number of identical or different groups R$^c$:

R$^c$, which may be the same or different to any other R$^c$, is halogen, hydroxyl, nitro, CN, carboxyl, C$_1$-C$_4$-alkyl, C$_2$-C$_4$-alkenyl, C$_2$-C$_8$-alkynyl, C$_1$-C$_4$-haloalkyl, C$_1$-C$_4$-alkoxy, C$_1$-C$_4$-haloalkoxy, C$_1$-C$_6$-alkoxyimino-C$_1$-C$_4$-alkyl, C$_2$-C$_6$-alkenyloxyimino-C$_1$-C$_4$-alkyl, C$_2$-C$_6$-alkynyloxyimino-C$_1$-C$_4$-alkyl, C$_1$-C$_6$-alkoxyimino-, C$_2$-C$_6$-alkenyloxyimino-, C$_2$-C$_6$-alkynyloxyimino-, C$_2$-C$_6$-haloalkenyloxyimino-, C$_3$-C$_6$-cycloalkyl, C$_3$-C$_6$-cycloalkenyl, phenyl or a 5-membered saturated, partially unsaturated or aromatic heterocyclyl which, in addition to carbon atoms, contains one to three heteroatoms from the group consisting of N, O and S as ring members; wherein the aforementioned cyclic groups R$^c$ are attached via a direct bond, an oxygen or sulfur atom, and where the aliphatic or cyclic groups R$^c$ for their part may carry 1, 2, 3 or up to the maximum possible number of identical or different groups R$^d$:

R$^d$, which may be the same or different to any other R$^d$, is halogen, C$_1$-C$_4$-alkyl or C$_1$-C$_4$-haloalkyl;

or

R$^3$ is —CR$^A$=N—O—R$^B$, wherein

R$^A$ is amino, hydroxyl, C$_1$-C$_4$-alkyl, C$_2$-C$_4$-alkenyl, C$_2$-C$_4$-alkynyl, C$_1$-C$_4$-halo-alkyl, C$_1$-C$_4$-alkoxy, C$_1$-C$_4$-haloalkoxy, C$_3$-C$_6$-cycloalkyl, C$_3$-C$_6$-cycloalkenyl, C$_2$-C$_6$-alkenyloxy, C$_3$-C$_6$-alkynyloxy, C$_1$-C$_4$-alkoxyimino-C$_1$-C$_4$-alkyl, C$_1$-C$_4$-alkylamino, C$_1$-C$_4$-alkoxycarbonyl, C$_1$-C$_4$-alkylcarbonyloxy, phenyl, phenyl-C$_1$-C$_4$-alkyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members; and wherein the aforementioned cyclic R$^A$ are attached via a direct bond, an oxygen or sulfur atom;

R$^B$ is C$_1$-C$_4$-alkyl, C$_2$-C$_4$-alkenyl, C$_2$-C$_4$-alkynyl, C$_1$-C$_4$-haloalkyl, C$_3$-C$_6$-cyclo-alkyl, C$_3$-C$_6$-cycloalkenyl, C$_1$-C$_4$-alkoxyimino-C$_1$-C$_4$-alkyl, C$_1$-C$_4$-alkoxy-carbonyl, phenyl, phenyl-C$_1$-C$_4$-alkyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members;

where the aliphatic or cyclic groups R$^A$ and/or R$^B$ for their part may carry 1, 2, 3 or up to the maximum possible number of identical or different groups R$^e$:

R$^e$, which may be the same or different to any other R$^e$, is halogen, hydroxyl, nitro, CN, carboxyl, C$_1$-C$_4$-alkyl, C$_2$-C$_4$-alkenyl, C$_2$-C$_8$-alkynyl, C$_1$-C$_4$-haloalkyl, C$_1$-C$_4$-alkoxy or C$_1$-C$_4$-haloalkoxy;

to yield a (Z,2E)-5-cyclyloxy-2-methoxyimino-N-substituted-pent-3-enamide of formula VI.

10. Compounds of formula I and compounds of IV

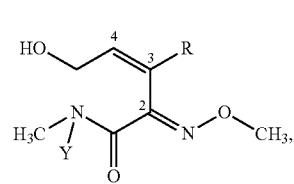

I

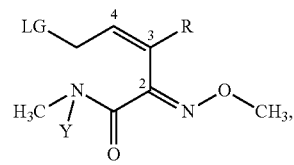

IV wherein

R is C$_1$-C$_4$-alkyl, C$_1$-C$_4$-haloalkyl, C$_3$-C$_6$-cycloalkyl or C$_3$-C$_6$-cycloalkyl-C$_1$-C$_4$-alkyl;

Y is hydrogen, C$_1$-C$_4$-alkoxy, C$_2$-C$_4$-alkenyl or benzyl; and wherein the —CH$_2$—OH group and the —C(=NOCH$_3$)C(=O)NYCH$_3$ group are on the same side of the C=C double bond between the carbon atoms depicted with the numbers 3 and 4 (Z-configuration), and wherein the —OCH$_3$ group and the —C(=O)NYCH$_3$ group are on the opposite side of the C=N double bond between the carbon atom depicted with number 2 and the neighbouring nitrogen atom (E-configuration);

and for compounds of formula IV, in addition:
LG is a leaving group selected from
halogen,
C$_1$-C$_6$-alkylsulfonyloxy, wherein alkyl is unsubstituted or substituted by 1, 2, 3, 4 or 5 halogen substituents, and
phenylsulfonyloxy, wherein phenyl is unsubstituted or is substituted by 1, 2, 3, 4 or 5 substituents selected from halogen, C$_1$-C$_6$-alkyl, C$_1$-C$_6$-haloalkyl, C$_1$-C$_6$-haloalkoxy and cyclopropyl.

11. Compounds of formula II

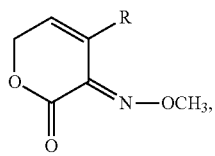

II wherein
R is C$_1$-C$_4$-alkyl, C$_1$-C$_4$-haloalkyl, C$_3$-C$_6$-cycloalkyl or C$_3$-C$_6$-cycloalkyl-C$_1$-C$_4$-alkyl.

12. A process for preparing 5-methoxyimino-2H-pyran-6-one compounds of formula II

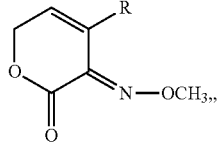

II wherein
R is C$_1$-C$_4$-alkyl, C$_1$-C$_4$-haloalkyl, C$_3$-C$_6$-cycloalkyl or C$_3$-C$_6$-cycloalkyl-C$_1$-C$_4$-alkyl;
the process comprising:
a) reacting a compound of formula VII

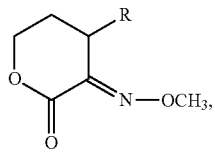

VII wherein R is as defined above;
with a free-radical halogenating agent in an organic solvent to obtain intermediate compounds VIII

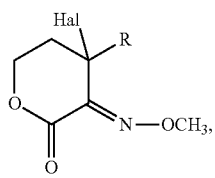

VIII wherein Hal is halogen and R is as defined above; and
b) after the first reaction step, treating the reaction mixture of step a) or compounds VIII with at least one base to obtain compounds II.

13. A process for preparing compounds of formula VII

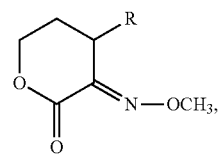

VII wherein
R is C$_1$-C$_4$-alkyl, C$_1$-C$_4$-haloalkyl, C$_3$-C$_6$-cycloalkyl or C$_3$-C$_6$-cycloalkyl-C$_1$-C$_4$-alkyl;
the process comprising:
a) reacting a compound of formula VII

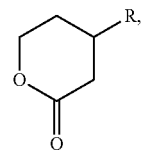

IX wherein R is defined as above;
with a nitrite in presence of Ag$_2$O;
and
b) after the first reaction step, treating the reaction mixture of step a) with at least one alkylating agent selected from iodomethane, chloromethane, bromomethane or dimethyl sulfate, to obtain compounds VII.

14. A process for preparing compounds of formula VII

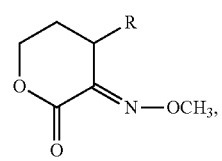

VII wherein
R is C$_1$-C$_4$-alkyl, C$_1$-C$_4$-haloalkyl, C$_3$-C$_6$-cycloalkyl or C$_3$-C$_6$-cycloalkyl-C$_1$-C$_4$-alkyl;
the process comprising:
a) reacting a compound of formula VII

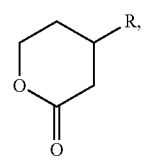

IX wherein R is defined as above;
with a nitrite in presence of at least one base;
and
b) after the first reaction step, treating the reaction mixture of step a) with at least one alkylating agent selected from iodomethane, chloromethane, bromomethane or dimethyl sulfate, to obtain a mixture of compounds VII and compounds VIIb

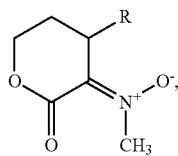

VIIb wherein R is defined as above;
and
c) after the second reaction step, treating the reaction mixture of step b) or compounds VIIb with methoxyamine or methoxyamine halogenide to obtain compounds VII.

15. The process of claim 1, wherein the compound of formula II

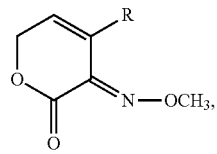

II wherein R is $C_1$-$C_4$-alkyl, $C_1$-$C_4$-haloalkyl, $C_3$-$C_6$-cycloalkyl or $C_3$-$C_6$-cyclo-alkyl-$C_1$-$C_4$-alkyl;
is prepared by:
a) reacting a compound of formula VII

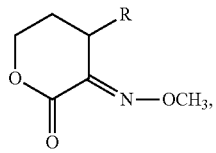

VII wherein R is as defined above;
with a free-radical halogenating agent in an organic solvent to obtain intermediate compounds VIII

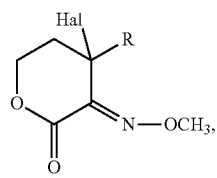

VIII wherein Hal is halogen and R is as defined above;
and
b) after the first reaction step, treating the reaction mixture of step a) or compounds VIII with at least one base to obtain compounds II.

16. The process of claim 15, wherein the compound of formula VII

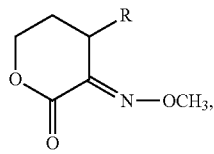

VII wherein
R is $C_1$-$C_4$-alkyl, $C_1$-$C_4$-haloalkyl, $C_3$-$C_6$-cycloalkyl or $C_3$-$C_6$-cycloalkyl-$C_1$-$C_4$-alkyl;
is prepared by:
a) reacting a compound of formula IX

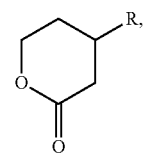

IX wherein R is defined as above;
with a nitrite in presence of $Ag_2O$;
and
b) after the first reaction step, treating the reaction mixture of step a) with at least one alkylating agent selected from iodomethane, chloromethane, bromomethane or dimethyl sulfate, to obtain compounds VII.

17. The process of claim 15, wherein the compound of formula VII

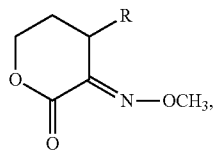

VII wherein
R is $C_1$-$C_4$-alkyl, $C_1$-$C_4$-haloalkyl, $C_3$-$C_6$-cycloalkyl or $C_3$-$C_6$-cycloalkyl-$C_1$-$C_4$-alkyl;
is prepared by:
a) reacting a compound of formula IX

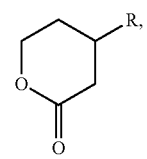

IX wherein R is defined as above;
with a nitrite in presence of at least one base;
and
b) after the first reaction step, treating the reaction mixture of step a) with at least one alkylating agent selected from iodomethane, chloromethane, bromomethane or dimethyl sulfate, to obtain a mixture of compounds VII and compounds VIIb

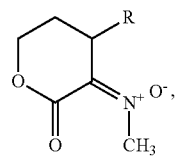
VIIb
wherein R is defined as above;
and
c) after the second reaction step, treating the reaction mixture of step b) or compounds VIIb with methoxyamine or methoxyamine halogenide to obtain compounds VII.
* * * * *